United States Patent [19]
Goshgarian

[11] 3,994,068
[45] Nov. 30, 1976

[54] ORTHODONTIC RETAINER
[76] Inventor: Robert A. Goshgarian, 1071 Ash Lawn, Lake Forest, Ill. 60045
[22] Filed: Nov. 19, 1975
[21] Appl. No.: 633,498

[52] U.S. Cl. .............................................. 32/14 E
[51] Int. Cl.² ........................................ A61C 14/00
[58] Field of Search ............ 32/7, 14 E, 14 D, 14 B

[56] References Cited
UNITED STATES PATENTS
1,139,170  5/1915  Drissler .............................. 32/14 E
1,142,467  8/1915  Walker ............................... 32/14 E
FOREIGN PATENTS OR APPLICATIONS
1,293,946  4/1969  Germany ............................ 32/14 E Primary Examiner—Robert Peshock
Attorney, Agent, or Firm—McWilliams & Mann

[57] ABSTRACT

An orthodontic retainer and retainer wire therefor in which the retainer wire is of one piece pre-formed construction and has a beam portion shaped and dimensioned lengthwise thereof to substantially conform to the chord extending between the points of contact of the upper jaw lateral incisors and the canine teeth adjacent same, together with consecutive vertical and horizontal open loops at each end of the beam portion with the horizontal loops merging into the retainer palatal extensions. The vertical and horizontal loops permit accurate adjustment of the wire beam portion for both tension and correct positioning on the labial side of the teeth. The wire is arranged for controlling the incisors and canines without having to be anchored to any of the teeth while providing for palatal extensions that are to be integrated with the palatal overlay, and that are located to avoid interference with the teeth on occlusion.

12 Claims, 9 Drawing Figures

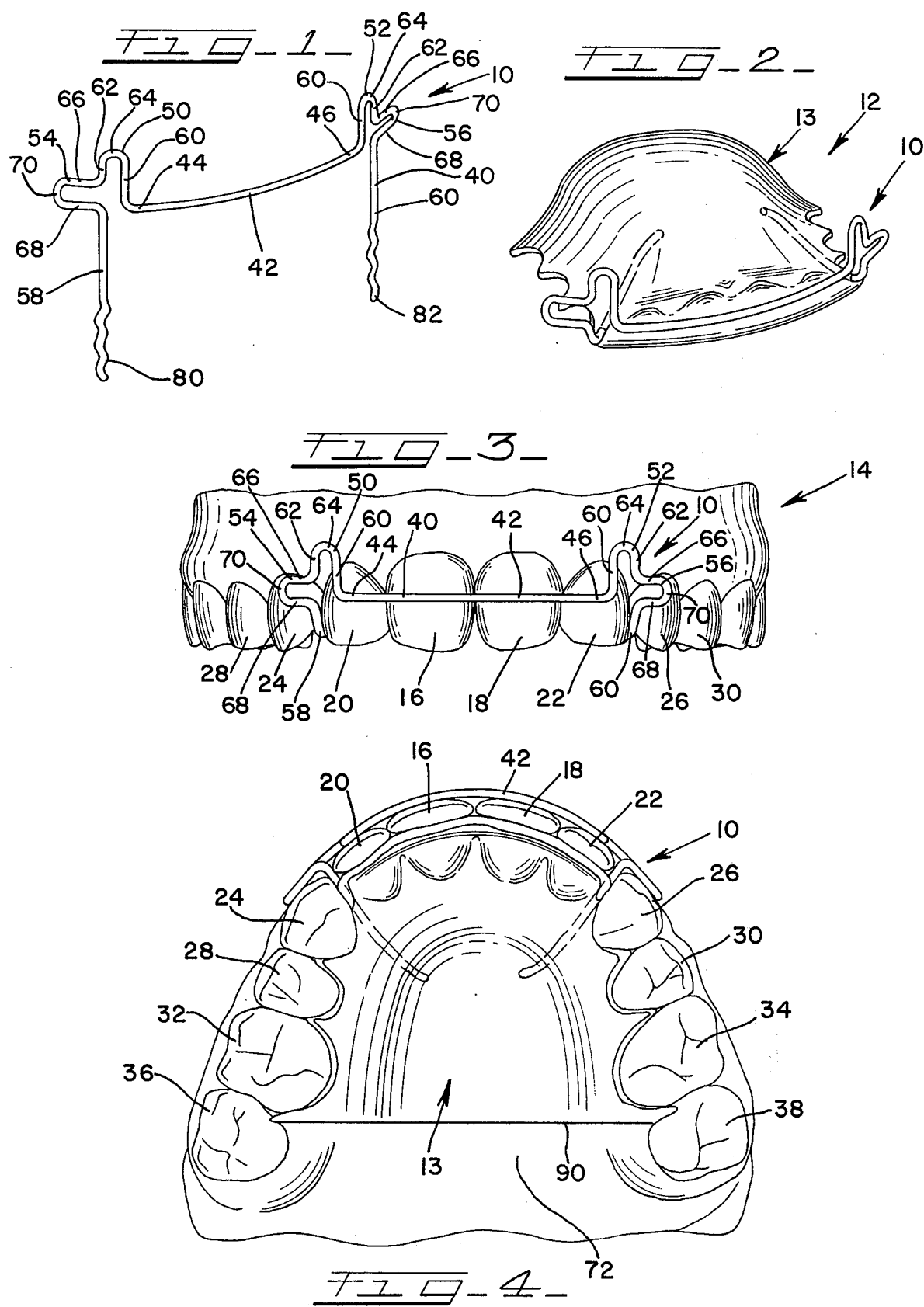

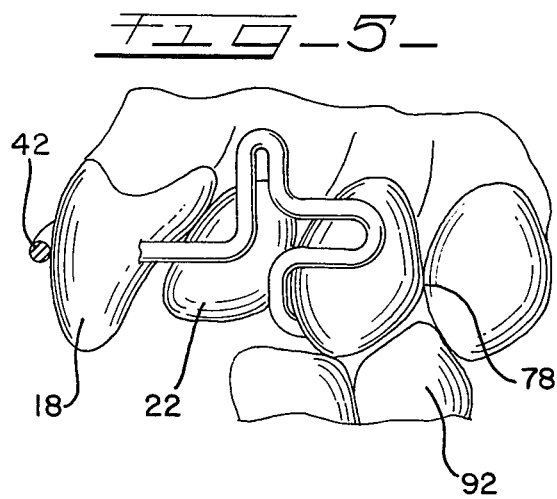
FIG-5-
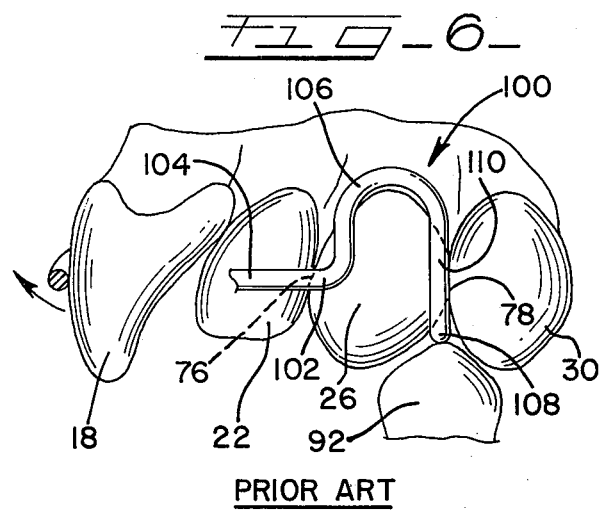
FIG-6-
PRIOR ART
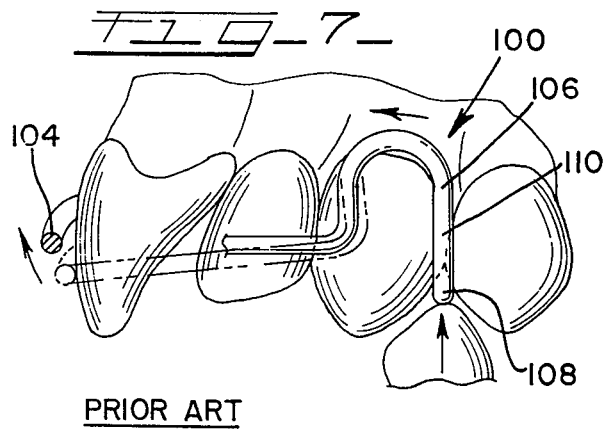
FIG-7-
PRIOR ART
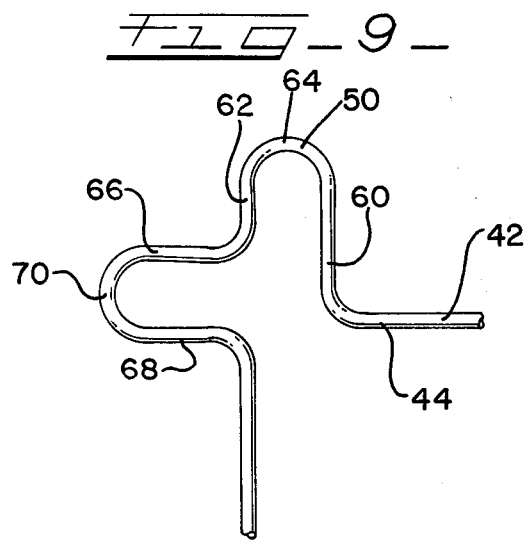
FIG-9-
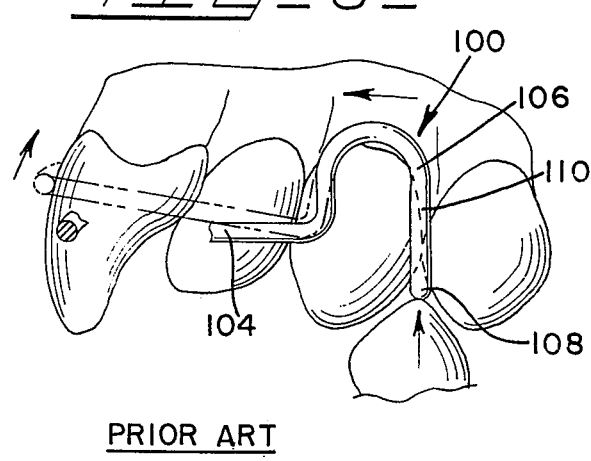
FIG-8-
PRIOR ART

ORTHODONTIC RETAINER

The present invention relates to orthodontic retainers, and more particularly, to retainers employed by orthodontists to control and maintain the upper or maxillary, anterior teeth in orthodontically treated cases, after the teeth have been positionally corrected.

Orthodontics is a specialty of dentistry dealing with the correction of positional irregularities of the teeth. The practice of this specialty involves the patient undergoing a series of procedures requiring, on the average, 24 to 30 months to complete.

These procedures involve a period of active treatment, during which positionally displaced teeth will be physically shifted, this usually being accomplished by the attachment of dimensionally slotted brackets to the permanent teeth, with biasing wires of appropriate cross section and outline, which have been bent to a predetermined form, being inserted into the brackets in question and secured in place. The so-called arch wires involved are configured and applied to transmit through the attachments to the teeth predetermined forces that act on the teeth to either tip them, or bodily carry the teeth, to predetermined positions that will dispose the teeth whose positions are being corrected in alignment with the normal arch or curve defined by the patient's jaw.

Active treatment on the teeth is customarily followed by a period of retention in which the teeth are positively maintained in their new positions until the teeth are in a state of equilibrium and balanced between the forces of the lip and cheek muscles under exterior side and the forces of the tongue on their interior sides. During the retention period the bone which supports the teeth may be in the most plastic state, and the teeth will be most responsive to peri-oral and intra-oral muscular forces that are normally unbalanced.

It has been standard practice for the patient to wear, during this period of retention, an orthodontic appliance, generally known as a retainer, that is fabricated by the orthodontist for this purpose and combines a retainer wire or wires and a formed palatal overlay which is to overlie the forward palate portion and envelope the lingual or inside half of all the upper teeth.

Most orthodontic retainers employ one or more wires in contact with the outer surfaces of the six anterior maxillary teeth to preclude these teeth from moving in a forward or outward direction under any unbalanced forces that may be acting on same, during the retention procedures. The retainer wire or wires are embedded in the plastic mass that conventionally forms the palatal overlay, this being provided for stabilizing the retainer wires employed and to maintain the general form of the dentition arch that has been achieved during the active treatment procedures, by offering mass and rigidity to the supporting bone in order to prevent the teeth from collapsing inwardly.

A familiar form of retainer wire widely used in connection with orthodontic retainers is represented by the familiar Hawley Labial retainer, which is usually characterized by a long horizontal beam portion extending variously from the permanent cuspid on one side of the incisors, across the incisors, to the permanent cuspid on the opposite side of the incisors, with the end portions or opposite terminals of the beam portion merging into high vertical open loops. Such loops each define anterior and posterior legs, with the anterior leg of each loop being formed at the contact of the permanent lateral incisor and its adjacent permanent cuspid and being directed vertically until approximately the junction of the cuspid with the gingival tissue, which the leg follows in a backward or distal direction maintaining the contour of the tissue to impart a curvature, and at the approximate contact with the next most distal or backward tooth (ordinarily the first bicuspid), the distal leg of the open vertical loop is formed. The retainer wire is then bent or deflected palatally, through the opening below the point of contact of the canine with the first bicuspid, for entry into the palatal overlay, whereby that portion of the wire becomes the palatal extension of the retainer wire. Both ends of the wire are formed in a similar but opposite manner. The beam portion of the retainer wire is disposed horizontally across the lip or labial surface of the anterior teeth involved, and as indicated, has the function of restraining any forward movement of these teeth. The high vertical loops at the retainer wire beam terminals are adjusted by opening or contracting the loops to provide a spring like effect on the wire horizontal beam to hold the beam in constant contact with the incisors. However, the location of the vertical open loops over the permanent cuspids results in the wire exercising no restraining effect on the canines. The conventional vertical loops are capable only of varying the tension in the beam, contraction of the loops resulting in increasing the force being applied to the incisor teeth, and opening of the loops reducing the biasing action of the beam on such teeth, or even releases contact with the teeth to permit them to drift forward.

These conventional retaining wires have been long known to have inherent defects of design which not only make them difficult to apply accurately, but also limit the effect their biasing or holding action on the teeth they engage to increasing or reducing the holding action on the incisors. They provide for no dimensional control of the canine teeth, and the location of the wire portions crossing rearwardly into the palatal extensions places the wires in a position to be engaged by the lower teeth on occlusion, which has the tendency to so stress the retainer appliance to tend to displace the entire upper dentition in a forward or outer direction. This tends to occur because the palatal extensions are forwardly biased on occlusion, due to the engagement on the wire by lower canines, which results in the forward bias on the wire palatal extensions tending to bias the palatal overlay as a whole against the lingual side of the upper teeth it engages so that all of the forward teeth are unduly biased outwardly, contrary to the very purpose of using orthodontic retainers in the first place.

While the Hawley labial wire is representative of one form of prior art retainer wire in substantial use, other forms are in substantial use which have similar limitations, and which also involve some manner of anchoring the wire to one or more of the patient's inner teeth on either side of the incisors, such as the canines and/or one of the molars. Various forms of multi piece retainer wire arrangements are available which involve soldering of the like during the process of fabricating the retainer, which renders the fabrication process time consuming, tedious and frequently inaccurate.

It is the Applicant's experience that the canine teeth are the focal point to be observed in repositioning of the teeth during the orthodontic active and retention treatment procedures. This is because the canine teeth are the key to good occlusion, and by correctly positioning the canine teeth in accordance with the desired dental arch, and the other teeth with respect thereto, the most beneficial occlusion can be obtained. It is therefore the Applicant's thesis that after the canine teeth have been correctly positioned, they should not be subjected to any forces that will displace same during the retention period, while at the same time, some means of gently retaining them in their adjusted positions against forward movement tendencies should be provided. Since the Hawley retainer tends to be outwardly biased by occlusion, it has the effect of outwardly shifting the canines from the positions they may have been disposed by the active treatment, for best occlusion purposes, which obviously tends to work against good results achieved during the active treatment.

A principal object of the present invention is to provide an orthodontic retainer which insures the retention function that is desired while avoiding application to the teeth retained of any biasing action, during occlusion or otherwise, that would tend to forwardly bias the teeth being retained.

Another principal object of the invention is to provide an orthodontic retainer device that avoids anchoring the retainer wire to any specific teeth and that has the retainer wire configured for accurate location of same relative to the coronal convexity of the incisors and application of desired retention pressures to the canines as well as to the incisors.

A further principal object of the invention is to provide a one piece pre-formed retainer wire for use in fashioning retainer appliances which is configured to apply active forces as desired to the incisors and the canine teeth without requiring specific anchoring to any of the maxillary teeth, while permitting accurate location of the beam portion of the wire across the incisors, and ready incorporation of the wire with the palatal overlay.

Still other important objects of the invention are to provide an orthodontic arrangement that is simple and effective of fabrication, to provide methods of making the retainer wire and retainer appliance of which the wire is to form a part, and to provide an orthodontic retainer that is economical of fabrication, simple to apply, and effective in use.

In accordance with the present invention, the orthodontic retainer wire is of pre-formed one piece construction shaped to have a beam portion proportioned lengthwise thereof for bracing engagement with the canines but extending short of the points of contact of the lateral incisors and the canine teeth adjacent same. At the end portions or terminals of the beam portion the wire is shaped to extend consecutively through vertical and horizontal open loops and thence into the palatal extension at each end of the wire. The vertical and open loops in combination provide adjustable spring devices for accurate positioning of the wire beam portion across the incisors as well as for tensioning same thereagainst. While the beam portion of the wire extends short of the canines, the horizontal loops are formed to project in overlying relation with the labial side of the canines for bracing relation therewith in a manner that can be controlled by bending of the horizontal loops inwardly or outwardly of the jaw.

Further in accordance with the invention, the orthodontic wire is preferably pre-formed to have the configuration indicated, with the palatal extensions being left in a straight line configuration substantially paralleling the legs of the vertical loops. The retainer wire may be made available in several different sizes, based on the length of the chord between the canines, as is best suited for application by orthodontists to their general range of patients.

With a supply of the orthodontic wires of this invention at hand, the orthodontist can select the size best suited for his patient and readily fabricate the retainer appliance, using as his work form the molded reproduction of the upper jaw that the orthodontist ordinarily will have on hand, and apply the retainer wire and palatal inlay forming material thereto, with the palatal overlay being formed, using suitable standard commercially available materials, to embed the retainer wire palatal extensions therein. The resulting appliance, which thus has been substantially perfectly form fitted to the model of the patient's jaw that is represented by the mold of the jaw, can then be easily removed and applied to the patient's jaw.

Still other objects, uses and advantages will be obvious or become apparent from a consideration of the following detailed description and the application drawings.

In the drawings:

FIG. 1 is a diagrammatic perspective view of a preferred form of retainer wire arranged in accordannce with the invention, shown ready for use by the orthodontist to make the retainer appliance contemplated by the present invention;

FIG. 2 is a diagrammatic perspective view showing a retainer appliance arranged in accordance with the invention, in which the retainer wire of FIG. 1 has been incorporated;

FIG. 3 is a front elevational view diagrammatically illustrating the upper jaw of a patient to which the appliance of FIG. 2 has been applied;

FIG. 4 is a bottom plan view of the upper jaw showing palatal area and the dental arch illustrating the appliance of FIG. 2 applied thereto;

FIG. 5 is a diagrammatic side elevational view, taken from the right hand side of FIG. 3, further illustrating the details of application of the orthodontic retainer wire to the patient's jaw, and also showing the approximate positioning of the lower canine and lateral incisor teeth relative to the upper canine and first bicuspid teeth, on occlusion;

FIG. 6, 7 and 8 are views similar to that of FIG. 5 but illustrating the jaw having the Hawley type retainer wire applied thereto, and the problems encountered on occlusion, and FIG. 9 is a fragmental plan view of one terminal or end portion of the retainer wire illustrating the specific shaping of the vertical and horizontal loops.

However, it is to be distinctly understood that the specific drawing illustrations provided have been supplied primarily with the requirements of the Patent Laws, and that the invention is susceptible of other embodiments, being readily apparent to those skilled in the art, and which are intended to be covered by the appended claims.

GENERAL DESCRIPTION

Reference numeral 10 of FIGS. 1 – 4 generally indicates a preferred form of retainer wire arranged in accordance with this invention, while reference numeral 12 indicates a retainer appliance in which the retainer wire 10 is incorporated with a palatal overlay 13, in accordance with the invention, for application to the upper jaw 14, and specifically to the maxillary teeth and adjacent palatal area, for use in practicing the retaining procedures of orthodontic treatment.

In the diagrammatic showings of FIGS. 3 and 4, the central incisor teeth of the upper jaw 14 are indicated by reference numerals 16 and 18, the lateral incisors are indicated by reference numerals 20 and 22, the canine teeth are indicated by reference numerals 24 and 26, the first bicuspids are indicated by reference numerals 28 and 30, the second bicuspids are indicated by reference numerals 32 and 34, and the first molars are indicated by reference numerals 36 and 38. The second and third molars that usually are part of the dental arch have been omitted to simplify illustration.

In accordance with the invention, the retainer wire 10 comprises a length 40 of suitable filamentous, resiliently flexibile material, such as or comparable to stainless steel, and preferably having a round cross-sectional configuration, shaped to define elongate beam portion 42 that at its end portions or terminals 44 and 46 is further formed to define the respective open vertical loops 50 and 52 and the open horizontal loops 54 and 56 which are in turn integral with palatal extensions 58 and 60.

The retainer wire 10 is given an arc substantially conforming to that of the dental arch (see FIG. 4).

As indicated, the wire 10 is preferably a pre-formed one piece component shaped as shown in FIG. 1. The vertical loops 50 are each defined by anterior legs 60 and posterior legs 62 that are integral with the loop bight portion 64. The loops 54 and 56 are each formed by an upper leg 66 and a lower leg 68, which are integral with the loop bight portion 70. The lower legs 68 of the respective horizontal loops are integral with the respective palatal extensions 58 and 60.

The retainer wire 10 is integrated with the palatal overlay 13, by fitting the retainer wire 10 on the mold 14, and specifically on the incisor and canine teeth thereof in the manner indicated in FIGS. 3 – 5, and as more specifically described hereinafter, and the palatal overlay 13, which comprises a layer of suitable plastic material, such as methyl methacrylate or other appropriate acrylic compound, is formed in place on the palatal portion of the mold of jaw 14 that is a duplicate of the jaw palate area indicated at 72 in FIG. 4. As part of the procedure of applying the wire 10 to the mold the palatal extensions 58 and 60 are shaped as indicated in FIGS. 2 and 4 to be covered by the integral with the palatal overlay 13.

When completed, the appliance 12 is thus mounted on a mold that is an exact duplicate of jaw 14 so that the appliance 12 can be lifted free of the mold and applied to jaw 14 with a snap fitting type action.

Further in accordance with the invention, the retainer wire 14 is proportioned such that its beam portion 42 extends short of the canine teeth 24 and 26, and the posterior legs of the vertical loops 50 and 52 are substantially aligned with the points of contact 76 between the lateral incisors and the canine teeth, on either side of the jaw. Further, the palatal extensions 58 and 60 are disposed in substantial alignment with the vertical loop legs 62, in the preformed embodiment of the wire 10, so that when the wire 10 is to be applied to the jaw 14 of the mold of same, the palatal extensions 58 and 60 may be turned inwardly of the teeth beneath the indicated points of contact 76, rather than the points of contact 78 between the canine teeth and the first bicuspids (as is conventional practice). This avoids lower tooth interference with the retainer wire on occlusion, as fully explained hereinafter.

The general arrangement of the retainer wire 10, in addition to its one piece pre-formed advantages, provides functions not heretofore available in comparable devices.

For instance, in giving the retainer wire 10 its final shape, vertical loops 50 and 52 and horizontal loops 54 and 56 may be adjusted, by expanding or contracting same, to both dispose the wire beam portion 42 at its most desirable location along the coronal convexity of the incisors (see FIG. 5), but also the beam portion 42 may be tensioned against or even spaced somewhat from the incisors as deemed desirable by the orthodontist. For this purpose, the vertical loops 50 and 52 are widened or contracted by using conventional orthodontist crimping implements to tighten or loosen the bearing action of the beam 42 against the incisors, while the horizontal loops 54 and 56 may be widened or narrowed, using similar crimping implements, to adjust the elevation of the wire beam portion 42 along the length of the incisors.

Furthermore, the horizontal loops 54 and 56 may be bent inwardly or outwardly of the teeth, as desired, to place a desired amount of restraint on the canine teeth 24 and 26 without, however, being anchored in any way to the canine teeth.

SPECIFIC DESCRIPTION

In accordance with one method of making the wire 10, a length of wire is selected from which the wire 10 is to be formed. Assuming that a mold has been made of the jaw 14, (as is customary practice), to which the appliance 12 is to be applied, the chord about the dental arch, between the contact points 76 on either side of the incisors, is measured and this may be most conveniently done by using the mold. This measurement determines the size of the retainer wire 10 to be used for that patient; in the final form, this distance will be the distance between the vertical loop posterior legs 62.

In practice, this distance will lie in the range of between about 32 to about 42 millimeters and may be called the inter-canine measurement.

The wire 10 is then shaped starting at one end of same to form a generally rectilinearly contoured palatal extension 60, the horizontal loop 56, the vertical loop 52, and the beam portion 42, followed by the second vertical loop 50, the second horizontal loop 54, and the palatal extension 58.

As indicated, the palatal extensions 58 and 60 are initially disposed in substantial alignment with the respective vertical loop legs 62. The end portions 80 and 82 of the respective palatal extensions may be given the indicated indented shape to insure good anchoring action of the palatal extensions within the palatal overlay 13.

The retainer wire is then arched in conformity with the dental arch (as indicated in FIG. 4), this also being done by using appropriate orthodontist tools.

In this connection, best results are obtained when the vertical loop bight portions are formed in semi-circular form having a diameter of approximately 0.075 inch, and the bight portion 70 of the horizontal loops are formed in semi-circular configuration having a diameter of approximately 0.050 inch. The legs 60 of the vertical loops should be approximately 5 millimeters while the legs 62 thereof should be approximately 3 millimeters. The legs 66 and 68 of the horizontal loops should be approximately 4 millimeters.

As previously indicated, it is convenient to have the retainer wire 10 available to the orthodontist in preforms in appropriate sizes whereby the retainer wire 10 would be in the form of FIG. 1 but having a length between the vertical loop legs 62 at selective intervals in the approximate 32 – 42 millimeter intercanine chord dimension rating that has been indicated. In any event, the orthodontist in fabricating a retainer appliance 12 either shapes a retainer wire 10 to substantially the form illustrated in FIG. 1, or selects a pre-formed wire of similar shape, in accordance with the intercanine measurement that has been made between the lateral incisor-canine points of contact 76 on either side of the incisors. The wire 10 is then fitted directly to the mold that has been made of the jaw 14, with the final adjustments being made with the orthodontist's conventional fitting tools to adjust the vertical or horizontal loops of the wire 10 to obtain the desired positioning of the beam portion 42, relative to the incisors, as has been previously referred to. The palatal extensions 58 and 60 as part of this procedure are angled rearwardly of the abutting lateral incisors and canines on either end of the wire and deformed to lie in substantial conformity to the palatal area defined by the mold on the jaw 14.

Also, as part of the adjustment procedure involved, the horizontal loops 54 and 56 are adjusted inwardly or outwardly of the teeth so as to apply the desired retaining action on the canine teeth.

The palatal overlay 13, is then formed in place by utilizing conventional equipment for this purpose, whereby a wafer of the plastic material from which the overlay is formed is subjected to heat and pressure which effects the plastic material being deformed into substantial conformity with the contours of the forward portion of the palatal cavity, against the lingual or inside half of the upper teeth. The deforming action involved also embeds the retainer wire palatal extensions in the palatal overlay.

Following conventional procedures, the orthodontist then suitably trims the overlay about its margins to define smooth contours along the back side of the teeth and the back edge 90 of the overlay as indicated in the drawings.

When the patient is to receive the retainer appliance 12, the appliance is removed from the jaw mold and makes a perfect snap fit engagement with the upper jaw of the patient to assume the positioning indicated in FIGS. 3 – 5.

The diagrammatic illustrations of the prior art Hawley device shown in FIGS. 6 – 8 indicate the adverse effect on that device due to engagement of the lower canine teeth 92 with same. In the showing of FIGS. 6 – 8, the Hawley retainer is indicated at 100 and comprises wire 102 formed to define beam portion 104, the vertical loops 106 at either end of the beam portion (although only one end is shown in these figures), with the vertical loops 106 each merging into palatal extensions 108 that are turned rearwardly of the teeth along the point of contact 78 of the canine teeth and the first bicuspids, for shaping and embedding in a palatal overlay in a manner similar to that described in connection with the overlay 13.

The retainer 100 has its beam portion 104 proportioned to, when the retainer wire is applied to the teeth, to project beyond the lateral incisors 20 and 22 so as to dispose the vertical loop 106 in the manner already described whereby the palatal extensions 108 may be turned over behind the teeth below the contact point 78.

FIG. 6 shows the passive condition in which the jaws have been moved towards occlusion so as to not put any upward pressure on the retainer 100. However, when the patient goes to complete occlusion, pressure is applied to the wire 100 at the juncture between the vertical loop leg 110 and the palatal extension 108 which has the effect shifting the wire 100, the retainer appliance of which it forms a part, and the canines and incisors forwardly, as indicated in FIGS. 7 and 8, as well as mislocating the wire 100.

Assuming that the vertical loop 106 of the retainer 100 has been adjusted, in mounting same, to dispose the retainer wire beam portion 104 in the desired position indicated in FIG. 6, this biasing action on the retainer wire 100 may tend to swing the retainer wire 100 counterclockwise to the broken line position of FIG. 7, wherein the retainer wire beam portion is too low on the incisor teeth. Efforts to correct the positioning of the retainer beam portion 104 by enlarging the vertical loop 106 will return the beam portion 104 to its desired elevation relative to the incisors, but the expanding of the loops 106 that is required to do this will leave the beam portion spaced from the incisors, with the result that retention of the incisors will be lost.

Should the occlusion tend to swing the retainer wire 100 counterclockwise, to the broken line position of FIG. 8, the retainer wire beam portion 104 would be too far up on the incisors. However, correction of this position of the retainer wire beam portion would not be feasible since contraction of the loop 76 to do this would locate the retainer wire beam portion within the projection of the incisors, as indicated in solid lines in FIG. 8.

The problems illustrated by FIGS. 6 – 8 are avoided in accordance with the present invention, as indicated by FIG. 5, it being pointed out that the tooth contact point 76 ordinarily somewhat higher or above the level of the contact points 78, and just enough to accommodate the passing of the retainer wire palatal extensions 58 and 60 rearwardly of the teeth of engagement by the lower teeth on occlusion, as indicated in FIG. 5.

It will therefore be seen that the invention provides a retainer wire and retainer appliance for using same that have a number of substantial advantages over prior practices.

For instance, the retainer wire requires no anchoring to any of the patient's teeth while permitting full integration with the palatal overlay by means of palatal extensions that are positioned to avoid interference with the retainer wire on occlusion by the lower teeth.

Furthermore, the combined vertical and horizontal loops of the retainer wire permit accurate adjustment of the positioning of the beam portion of the wire with respect to the outer surfaces of the incisors, both as to position and for biasing effect.

A further significant advantage is that the horizontal loops themselves may be adjusted inwardly and outwardly of the teeth to provide the desired restraining action on the canines, this action on the canines being available even though the retainer wire beam portion does not extend to the canines.

As the retainer wire beam portion is proportioned to overlie only the incisors, its length is significantly shortened over conventional retainers and thus the wire itself may be of lesser strength and corresponding less cross-sectional thickness to achieve the desired restraining action on the incisors. This facilitates rapid shaping of the wire to fit a patient's specific needs.

The resulting retainer provides full control over the four anterior maxillary teeth without having to bias the maxillary canine teeth for this purpose, and yet permitting a bracing action on the maxillary canine teeth as well.

By having the retainer wire of the invention in the single wire, pre-formed embodiment that has been referred to, the orthodontist is provided with the raw material to minimize retainer appliance fabrication while insuring optimum positioning of the retainer for fast restraining action on the anterior teeth. The orthodontist having pre-formed retainer wires 10 available to him in reasonable size selections can complete fabrication of a retainer appliance 12, ready for application to the patient, in 4 to 5 minutes.

The foregoing description and the drawings are given merely to explain and illustrate the invention and the invention is not to be limited thereto, except insofar as the appended claims are so limited, since those skilled in the art who have the disclosure before them will be able to make modifications and variations therein without departing from the scope of the invention.

I claim:

1. An orthodontic retainer appliance for application to the upper jaw of a patient in the area of the incisor and canine teeth, said appliance comprising:
  a palatal overlay shaped to complementarily fit against the palate portion adjacent said teeth,
  and a retainer member fixed to said overlay,
  said retainer member comprising:
  a wire formed from a resiliently flexible material and shaped to define:
  a beam portion arced to substantially conform with the labial side arch defined by the incisor and canine teeth,
  an open vertical loop at each end of the beam portion,
  an open horizontal loop at each end of the retainer member with said loops lying along the projected arc of said beam portion at the respective ends of said beam portion,
  and a palatal extension integral with each horizontal loop and anchored in said overlay,
  said retainer beam portion being proportioned to engage the labial side of the incisor teeth and short of the jaw canine teeth,
  said retainer member horizontal loop portions being proportioned to engage the labial side of the jaw canine teeth at either end of the retainer member,
  and said palatal extensions respectively projecting distally of the appliance adjacent the contacting portions of the jaw lateral incisor and canine teeth.

2. The appliance set forth in claim 1 wherein:
  said retainer member is of one piece construction extending consecutively from one of the palatal extensions through the horizontal and open loops and beam portion at one end of the retainer member to the other palatal extension consecutively through the beam portion, and the vertical and horizontal loops at the other end of the retainer member.

3. The appliance set forth in claim 1 wherein:
  said horizontal loops extend in opposition along the arc of said retainer member and beyond the ends of said beam portion.

4. An orthodontic retainer appliance for application to the upper jaw of a patient in the area of the incisor and canine teeth, in which said appliance includes a palatal overlay shaped to complementarily fit against the palate portion adjacent said teeth, and a retainer member fixed to said overlay, the improvement wherein said retainer member comprises:
  a wire formed from a resiliently flexible material and shaped to define:
  a beam portion arced to substantially conform with the labial side arc defined by the incisor and canine teeth,
  an open vertical loop at each end of the beam portion,
  an open horizontal loop at each end of the retainer member with said loops lying along the projected arc of said beam portion at the respective ends of said beam portion,
  and a palatal extension integral with each horizontal loop and anchored in said overlay,
  said retainer beam portion being proportioned to engage the labial side of the incisor teeth and short of the jaw canine teeth,
  said retainer member horizontal loop portions being proportioned to engage the labial side of the jaw canine teeth at either end of the retainer member,
  and said palatal extensions respectively projecting distally of the appliance adjacent the contacting portion of the jaw lateral incisor and canine teeth.

5. The improvement set forth in claim 4 wherein:
  said retainer member is of one piece construction extending consecutively from one of the palatal extensions through the horizontal and open loops and beam portion at one end of the retainer member to the other palatal extension consecutively through the beam portion, and the vertical and horizontal loops at the other end of the retainer member.

6. The improvement set forth in claim 4 wherein:
  said horizontal loops extend in opposition along the arc of said retainer member and beyond the ends of said beam portion.

7. The improvement set forth in claim 4 wherein:
  said palatal extensions are formed to be free of anchoring connection to the patient's teeth.

8. A preformed orthodontic retainer member for use in making an orthodontic retainer appliance for application to the upper jaw of a patient in the area of the incisor and canine teeth, which appliance is to include a palatal overlay shaped to complementarily fit against the palatal portion adjacent said teeth, said retainer member comprising:
  a one piece filamentous element formed from a stiff, resliently bendable material and shaped to define:
  a beam portion arced to substantially conform with the labial side arc defined by human upper jaw incisor and canine teeth,
  an open vertical loop at each end of said beam portion,
  an open horizontal loop at each end of the retainer member with said loops lying along the projected arc of said beam portion at the respective ends of said beam portion,
  and a palatal extension integral with each horizontal loop and anchored in said overlay, said retainer member horizontal loop portions extending away from their respective ends of said beam portion for application against the labial side of the jaw canine teeth when the appliance is applied to the upper jaw, said palatal extensions projecting in substantial parallelism to the planes of the respective vertical loops and being separated respectively therefrom, at each end of said beam portion, by the respective horizontal loops.

9. The retainer member set forth in claim 8 wherein: said material is stainless steel.

10. The retainer member set forth in claim 8 wherein: said vertical loops have their bight portions defining semicircles having a diameter of approximately 0.075 inch, and said horizontal loops have their bight portions defining semicircles having a diameter of approximately 0.050 inch.

11. The method of making an orthodontic retainer member for use in making an orthodontic retainer appliance for application to the upper jaw of a patient in the area of the incisor and canine teeth, said method comprising:

determining the chord length between the points of contact of the two lateral incisor teeth with the canine teeth adjacent same, taking a length of wire, forming in the wire a beam portion having a length approximating the chord length and bending the wire at the beam end portion ends to consecutively define along the wire extending from the respective beam end portions a first open loop projecting normally of the beam portion and a second oppen loop substantially paralleling the beam portion merging into palatal extensions paralleling said first open loops.

12. The method set forth in claim 11 including: arcing the beam portion and first loops into substantial conformity to the chord.

* * * * *